(12) United States Patent
Stahmann et al.

(10) Patent No.: US 8,032,208 B2
(45) Date of Patent: *Oct. 4, 2011

(54) SYSTEM AND METHOD FOR DISPLAYING A HISTOGRAM OF CARDIAC EVENTS

(75) Inventors: Jeffrey E. Stahmann, Ramsey, MN (US); Rene H. Wentkowski, Berlin (DE); James Kalgren, Lino Lakes, MN (US); Par Lindh, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 564 days.

This patent is subject to a terminal disclaimer.

(21) Appl. No.: 12/169,432

(22) Filed: Jul. 8, 2008

(65) Prior Publication Data

US 2008/0269827 A1     Oct. 30, 2008

Related U.S. Application Data

(63) Continuation of application No. 11/115,618, filed on Apr. 27, 2005, now Pat. No. 7,406,348, which is a continuation of application No. 09/738,868, filed on Dec. 15, 2000, now Pat. No. 6,941,167.

(51) Int. Cl.
A61B 5/044     (2006.01)

(52) U.S. Cl. ......................................................... 600/523

(58) Field of Classification Search .................... 600/523
See application file for complete search history.

(56) References Cited

U.S. PATENT DOCUMENTS

| | | | |
|---|---|---|---|
| 4,316,249 A | 2/1982 | Gallant et al. | |
| 4,364,397 A * | 12/1982 | Citron et al. | 600/523 |
| 4,549,552 A | 10/1985 | Groch et al. | |
| 4,809,697 A | 3/1989 | Causey, III et al. | |
| 4,825,869 A | 5/1989 | Sasmor et al. | |
| 4,964,410 A | 10/1990 | Leahey et al. | |
| 5,113,869 A | 5/1992 | Nappholz et al. | |
| 5,217,021 A | 6/1993 | Steinhaus et al. | |
| 5,311,874 A | 5/1994 | Baumann et al. | |

(Continued)

FOREIGN PATENT DOCUMENTS

EP     0565084 A2     10/1993

(Continued)

OTHER PUBLICATIONS

*Vigor Model 2950 Physician's System Manual*, © 1996Cardiac Pacemakers (CPI), (1996), 87 pgs.

(Continued)

*Primary Examiner* — Kennedy Schaetzle

(74) *Attorney, Agent, or Firm* — Schwegman, Lundberg & Woessner, P.A.

(57) ABSTRACT

Systems, devices and methods are provided for displaying statistical distributions of cardiac events. A device embodiment comprises circuitry adapted to communicate with a medical device that is adapted to acquire data regarding cardiac events occurring at two or more cardiac sites, and display means for displaying a histogram of the data as two or more statistical distributions for the two or more cardiac sites. The histogram includes a number of histogram bins. At least one of the histogram bins includes both a representation for at least a portion of a statistical distribution of a cardiac event for a first cardiac site and a representation for at least a portion of a statistical distribution of a cardiac event for a second cardiac site. Other embodiments are provided herein.

24 Claims, 11 Drawing Sheets

U.S. PATENT DOCUMENTS

| | | | |
|---|---|---|---|
| 5,487,755 A | 1/1996 | Snell et al. | |
| 5,507,786 A | 4/1996 | Morgan et al. | |
| 5,513,645 A | 5/1996 | Jacobson et al. | |
| 5,549,654 A | 8/1996 | Powell | |
| 5,578,063 A | 11/1996 | Bocek et al. | |
| 5,603,331 A | 2/1997 | Heemels et al. | |
| 5,722,999 A | 3/1998 | Snell | |
| 5,891,178 A | 4/1999 | Mann et al. | |
| 5,948,005 A | 9/1999 | Valikai et al. | |
| 5,974,341 A | 10/1999 | Er et al. | |
| 5,978,707 A | 11/1999 | Krig et al. | |
| 6,016,442 A | 1/2000 | Hsu et al. | |
| 6,016,446 A | 1/2000 | Belalcazar | |
| 6,067,471 A | 5/2000 | Warren | |
| 6,076,015 A | 6/2000 | Hartley et al. | |
| 6,091,990 A | 7/2000 | Hsu et al. | |
| 6,108,577 A | 8/2000 | Benser | |
| 6,112,117 A | 8/2000 | KenKnight et al. | |
| 6,240,317 B1 | 5/2001 | Villaseca et al. | |
| 6,253,102 B1 | 6/2001 | Hsu et al. | |
| 6,289,244 B1 | 9/2001 | Conley et al. | |
| 6,289,248 B1 | 9/2001 | Conley et al. | |
| 6,301,503 B1 | 10/2001 | Hsu et al. | |
| 6,308,095 B1 | 10/2001 | Hsu et al. | |
| 6,312,378 B1 | 11/2001 | Bardy | |
| 6,415,175 B1 | 7/2002 | Conley et al. | |
| 6,418,340 B1 | 7/2002 | Conley et al. | |
| 6,449,504 B1 | 9/2002 | Conley et al. | |
| 6,459,929 B1 | 10/2002 | Hopper et al. | |
| 6,459,934 B1 | 10/2002 | Kadhiresan | |
| 6,535,763 B1 | 3/2003 | Hiebert et al. | |
| 6,665,558 B2 | 12/2003 | Kalgren et al. | |
| 6,718,198 B2 | 4/2004 | Conley et al. | |
| 6,721,594 B2 | 4/2004 | Conley et al. | |
| 6,941,167 B2 | 9/2005 | Stahmann et al. | |
| 7,047,065 B2 | 5/2006 | Kalgren et al. | |
| 7,406,348 B2 | 7/2008 | Stahmann et al. | |
| 7,844,322 B2 | 11/2010 | Kalgren et al. | |
| 2002/0077859 A1 | 6/2002 | Stahmann et al. | |
| 2003/0114891 A1 | 6/2003 | Hiebert et al. | |
| 2004/0082976 A1 | 4/2004 | Kalgren et al. | |
| 2005/0187588 A1 | 8/2005 | Stahmann et al. | |
| 2006/0189877 A1 | 8/2006 | Kalgren et al. | |
| 2011/0046692 A1 | 2/2011 | Kalgren et al. | |

FOREIGN PATENT DOCUMENTS

| | | | |
|---|---|---|---|
| EP | 0711531 A1 | 5/1996 | |

OTHER PUBLICATIONS

"U.S. Appl. No. 09/738,858, filed Jan. 23, 2004 to Final Office Action mailed Nov. 26, 2003", 14 pgs.

"U.S. Appl. No. 09/738,868, Final Office Action mailed Nov. 26, 2003", 7 pgs.

"U.S. Appl. No. 09/738,868, Non-Final Office Action mailed Apr. 15, 2004", 7 pgs.

"U.S. Appl. No. 09/738,868, Final Office Action mailed Oct. 5, 2004", 6 pgs.

"U.S. Appl. No. 09/738,868, Advisory Action mailed Feb. 13, 2004", 2 pgs.

"U.S. Appl. No. 09/738,868, Non-Final Office Action mailed Jul. 17, 2003", 7 pgs.

"U.S. Appl. No. 09/738,868, Notice of Allowance mailed Jan. 13, 2005", 6 pgs.

"U.S. Appl. No. 09/738,868, Request for Continued Examination mailed Feb. 24, 2004", 1 pg.

"U.S. Appl. No. 09/738,868, filed Oct. 15, 2003 to Non-Final Office Action mailed Jul. 17, 2003", 15 pgs.

"U.S. Appl. No. 09/738,868, filed Dec. 6, 2004 to Final Office Action mailed Oct. 5, 2004", 17 pgs.

"U.S. Appl. No. 09/738,868, filed Jun. 9, 2004 to Non-Final Office Action mailed Apr. 15, 2004", 14 pgs.

"U.S. Appl. No. 11/115,618, Non-Final Office Action mailed Mar. 12, 2007", 10 pgs.

"U.S. Appl. No. 11/115,618, Notice of Allowance mailed Apr. 2, 2008", 4 pgs.

"U.S. Appl. No. 11/115,618, filed Oct. 22, 2007 to Final Office Action mailed Aug. 24, 2007", 15 pgs.

"U.S. Appl. No. 11/115,618, filed Mar. 4, 2008 to Final Office Action mailed Jan. 8, 2008", 9 pgs.

"U.S. Appl. No. 11/115,618, filed Jun. 12, 2007 to Non-Final Office Action mailed Mar. 12, 2007", 13 pgs.

"U.S. Appl. No. 11/115,618, Final Office Action mailed Aug. 24, 2007", 11 pgs.

"U.S. Appl. No. 11/115,618, Final Office Action mailed Jan. 8, 2008", 5 pgs.

\* cited by examiner

SYSTEM AND METHOD FOR DISPLAYING A HISTOGRAM OF CARDIAC EVENTS

CROSS-REFERENCE TO RELATED APPLICATION(S)

This application is a continuation of U.S. patent application Ser. No. 11/115,618, filed on Apr. 27, 2005, now issued as U.S. Pat. No. 7,406,348, which is a continuation of U.S. patent application Ser. No. 09/738,868, filed on Dec. 15, 2000, now issued as U.S. Pat. No. 6,941,167, the specifications of which are incorporated herein by reference.

FIELD OF THE INVENTION

This invention relates generally to the field of medical devices, and more particularly to systems and methods for graphically displaying cardiac events.

BACKGROUND

Medical devices, including cardiac stimulus devices such as implantable cardiac pacemakers and implantable cardioverter defibrillators (ICDs), are surgically implanted within a patient. Cardiac stimulus devices have one or more electrical leads with one or more electrodes that conduct signals to and receive signals from the patient's heart. These lead(s) and their electrode(s) are placed in or around the heart. Each of the electrodes may be configured either to produce or pace a cardiac event, or to detect or sense an intrinsic cardiac event. Some medical devices record or otherwise collect these cardiac events.

A programming device or programmer communicates with the medical device through a communication link. The collected data regarding the paced and sensed cardiac events is transferred from the medical device to the programmer through the communication link. One example of a communication link is a telemetry link that provides means for commands and data to be non-invasively transmitted and received between the programmer and the device.

Medical devices collect more cardiac events at more cardiac sites as they provide more leads, electrodes per lead, and programming parameters for the leads. Thus, there is a greater need to present these cardiac events in a meaningful manner for comparison. For example, in the case of heart failure resynchronization, there is a need to determine how often a patient needs therapy and how often the patient is receiving therapy. Heart failure therapy relies on providing programmed paced cardiac events in a chamber or combination of chambers, and failure to deliver these programmed paces is viewed as therapy failure. It is important to provide the clinician with diagnostics that reveal the loss of therapy as well as the reason for the loss of therapy. Based on this information, the clinician attempts to optimize the operation of the medical device for a particular patient by adjusting programmable parameters in the medical device.

Therefore, there is a need in the art to provide a system and method for displaying cardiac events in a meaningful manner.

SUMMARY OF THE INVENTION

The present subject matter addresses the aforementioned problems by providing a display that can be used to view and compare cardiac events that occurred at two or more cardiac sites. More particularly, the present subject matter displays data from two or more sites of a heart in a graph as two or more statistical distributions for the two or more sites.

One aspect provides a programmer device that generally comprises circuitry for communicating with a medical device and a display. The medical device collects data regarding cardiac events that occurred at two or more cardiac sites. For example, the medical device collects data from two or more electrodes distributed in a single cardiac chamber and/or distributed in separate cardiac chambers. These cardiac events at these sites are represented in the display. The display provides a graph of the data as two or more statistical distributions for the two or more sites. In one embodiment, the graph is a histogram that generally comprises a plurality of histogram bins. Each of these histogram bins includes statistical distributions of cardiac events, and generally includes a first cardiac event distribution and a second cardiac event distribution. The first cardiac event distribution represents or displays cardiac events that occurred at a first cardiac site, and the second cardiac event distribution represents or displays cardiac events that occurred at a second cardiac site. According to one embodiment, the histogram provides both a right ventricular cardiac event distribution and a left ventricular cardiac event distribution in these histogram bins.

In one embodiment, the first cardiac event distribution is adjacent to the second cardiac event distribution in these histogram bins. In an alternative embodiment, the histogram further comprises a histogram axis that extends through each of the histogram bins. The first and second cardiac event distributions are on opposing sides of this histogram axis. In either of these embodiments, the cardiac events that occurred at these two sites are presented in a meaningful manner as statistical or frequency distributions in a graph that assists a viewer in comparing these cardiac events to, for example, evaluate a therapy. According to one embodiment, the first and second cardiac event distributions each provide distributions for both sensed intrinsic cardiac events and paced cardiac events. The first and second cardiac event distributions are distinguished using different colors, and the sensed and paced cardiac event distributions are distinguished using different fillings.

Another aspect provides a system that generally comprises a medical device and a programmer. The medical device, such as a pacemaker or defibrillator, collects data regarding cardiac events that occurred at two or more cardiac sites. The programmer communicates with the medical device, retrieves the data, and displays the data in a graph as two or more statistical distributions for the two or more sites. According to one embodiment, the graph is a histogram that includes a right ventricular cardiac event distribution and a left ventricular cardiac event distribution.

Another aspect provides a histogram for representing cardiac events that occur at two or more cardiac sites. The histogram generally comprises a plurality of histogram bins for the two or more statistical distributions. Each of the histogram bins generally includes at least a first cardiac event distribution and a second cardiac event distribution. The first cardiac event distribution represents or displays cardiac events that occurred at a first cardiac site, and the second cardiac event distribution represents or displays cardiac events that occurred at a second site. According to one embodiment, the first cardiac event distribution is a right ventricular cardiac event distribution, and the second cardiac event distribution is a left ventricular cardiac event distribution.

Another aspect provides a computer-readable medium encoded with a software program. The software program provides statistical distributions for two or more cardiac sites. The software program retrieves data regarding cardiac events occurring at these sites. According to one embodiment, the cardiac events are represented in a plurality of histogram bins in which each bin includes a first and second cardiac event distribution.

Another aspect provides a method that generally comprises retrieving data regarding cardiac events that occurred or are occurring at two or more sites, and displaying the data in a graph as two or more statistical distributions for the two or more sites. According to one embodiment, displaying the data comprises providing a histogram having a plurality of histogram bins for the distributions, and providing a first cardiac event distribution and a second cardiac event distribution. The first cardiac event distribution represents cardiac events that occurred at a first site, and the second cardiac event distribution represents cardiac events that occurred at a second site. According to one embodiment, the histogram includes a left ventricular cardiac event distribution and a right ventricular cardiac event distribution. Also, according to one embodiment, the statistical distribution includes sensed intrinsic cardiac events and paced cardiac events.

In one embodiment, the two or more sites include: at least one left ventricle site and at least one right ventricle site; at least two left ventricle sites; at least two right ventricle sites; at least one left atrium site and at least one right atrium site; at least two left atrium sites; at least two right atrium sites; at least two sites in a first ventricle and at least one site in a second ventricle; or at least two sites in a first atrium and at least one site in a second atrium. According to one embodiment, the cardiac event distribution displayed in the histogram is determined by dividing an event count in bin by a denominator. The denominator is the sum of a total primary site sense count, a total primary site pace count, and a total secondary pace count. The secondary pace count includes only secondary pacing events in which no primary pace is delivered for a corresponding cardiac cycle.

In the embodiments provided above, the inclusion of first and second statistical distributions does not preclude the inclusion of additional distributions; i.e. third, fourth, etc. distributions. Additionally, the inclusion of the first and second cardiac sites does not preclude the inclusion of additional cardiac sites in additional locations; i.e. third, fourth, etc. cardiac sites.

These and other aspects, features, embodiments and advantages of the invention will become apparent from the following description of the preferred embodiments of the invention.

DETAILED DESCRIPTION

In the following detailed description, references are made to the accompanying drawings that illustrate specific embodiments in which the invention may be practiced. Changes in the electrical, mechanical, structural, logical or programming designs may be made to the embodiments without departing from the spirit and scope of the present invention. The following detailed description is, therefore, not to be taken in a limiting sense and the scope of the present invention is defined by the appended claims and their equivalents.

The present subject matter addresses the aforementioned problems, and provides a graph of cardiac event data as two or more statistical distributions for the two or more sites. The graph allows a user to view and compare cardiac events at two or more cardiac sites in a meaningful manner. In one embodiment, the graph is a single histogram that generally comprises a plurality of histogram bins. The histogram bins represent cardiac events, and each of the histogram bins generally includes a first cardiac event distribution for cardiac events that occurred at a first site, and a second cardiac event distribution for cardiac events that occurred at a second site. Aspects of the present subject matter are provided herein.

Figure 1:
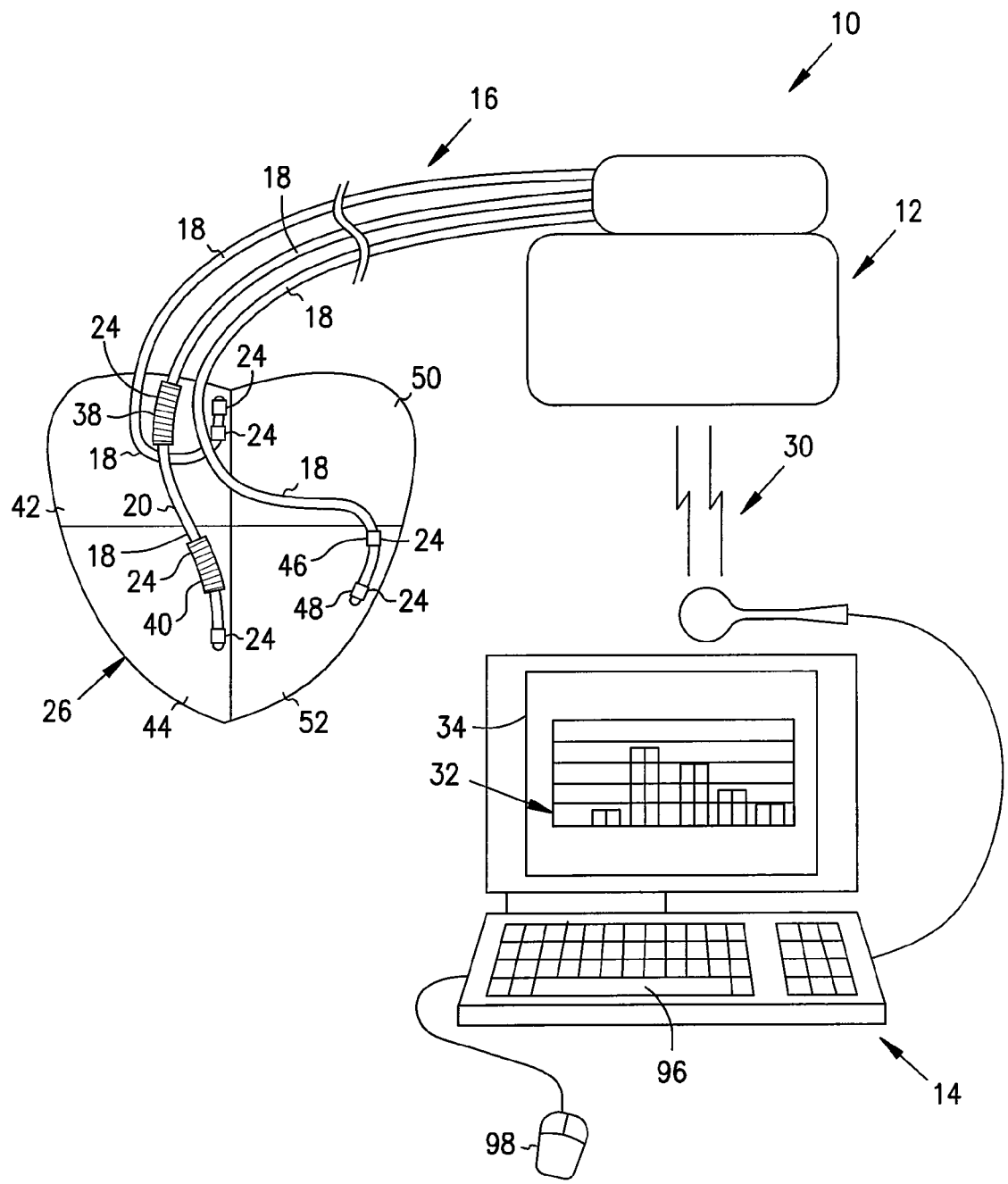
FIG. 1 is a schematic view of a system according to one embodiment.

One aspect, as illustrated in FIG. 1, is a cardiac rhythm management system 10. The system 10 generally comprises a medical device 12 and a programmer 14. The medical device 12 includes but is not limited to cardiac stimulation devices such as pacemakers and defibrillators. In addition to other functions, the medical device 12 collects data regarding cardiac events that occurred or are occurring at two or more cardiac sites, i.e. two or more locations in or around a heart.

The medical device 12 has an electrode system 16 comprised of at least one lead and at least one electrode 24 for each lead. FIG. 1 shows an example in which there are three leads 18. The illustrated leads 18 are inserted into a patient's heart 26. The electrodes 24 transmit electrical signals or paces to the heart 26 and receive or sense intrinsic electrical signals from the heart 26. The lead(s) 18 and electrode(s) 24 are arranged, programmed and/or otherwise configured in an attempt to optimize the operation of the medical device 12 for a particular patient.

The leads 18 and the electrodes 24 are physically arranged with respect to the heart 26 to properly transmit pace pulses and sense intrinsic signals from the heart 26. The medical device 12 is programmed to pace a cardiac event using a particular electrode or electrodes 24 and to sense a cardiac event using a particular electrode or electrodes 24. As such, the cardiac sites at which the cardiac events take place are determined by the position of the electrodes 24. For example, as generally shown in FIG. 1, a lead 18 may be inserted into the right atrium 42 and ventricle 44 so that an electrode 38 is positioned in the right atrium 42 and another electrode 40 is positioned in the right ventricle 44. A second lead 18 may be inserted through the coronary sinus and onto the left ventricle 52 (coronary sinus implant) so that electrodes 46 and 48 are positioned on the left ventricle 52, i.e. in the coronary vein located outside the ventricle, and form a dual electrode configuration for the left ventricle 52.

The medical device 12, with its electrode system 16, is adapted for collecting data regarding cardiac events occurring at two or more cardiac sites. In some variations or configurations, electrodes 24 are distributed among two or more of the chambers 42, 44, 50 and 52 of the heart 26. And in other variations, two or more electrodes 24 may be in a single chamber of the heart 26, such as in the left ventricle 52 as illustrated in FIG. 1. Therefore, a non-exclusive list of available variations of the positions of the electrodes 24, and thus the cardiac sites, include a first site in a first cardiac chamber and a second site in a second cardiac chamber, a first site and a second site in a first cardiac chamber, and a first site and a second site in a first cardiac chamber and a third site in a second cardiac chamber. In one embodiment, the two or more sites include: at least one left ventricle site and at least one right ventricle site; at least two left ventricle sites; at least two right ventricle sites; at least one left atrium site and at least one right atrium site; at least two left atrium sites; at least two right atrium sites; at least two sites in a first ventricle and at least one site in a second ventricle; or at least two sites in a first atrium and at least one site in a second atrium.

Figure 2:
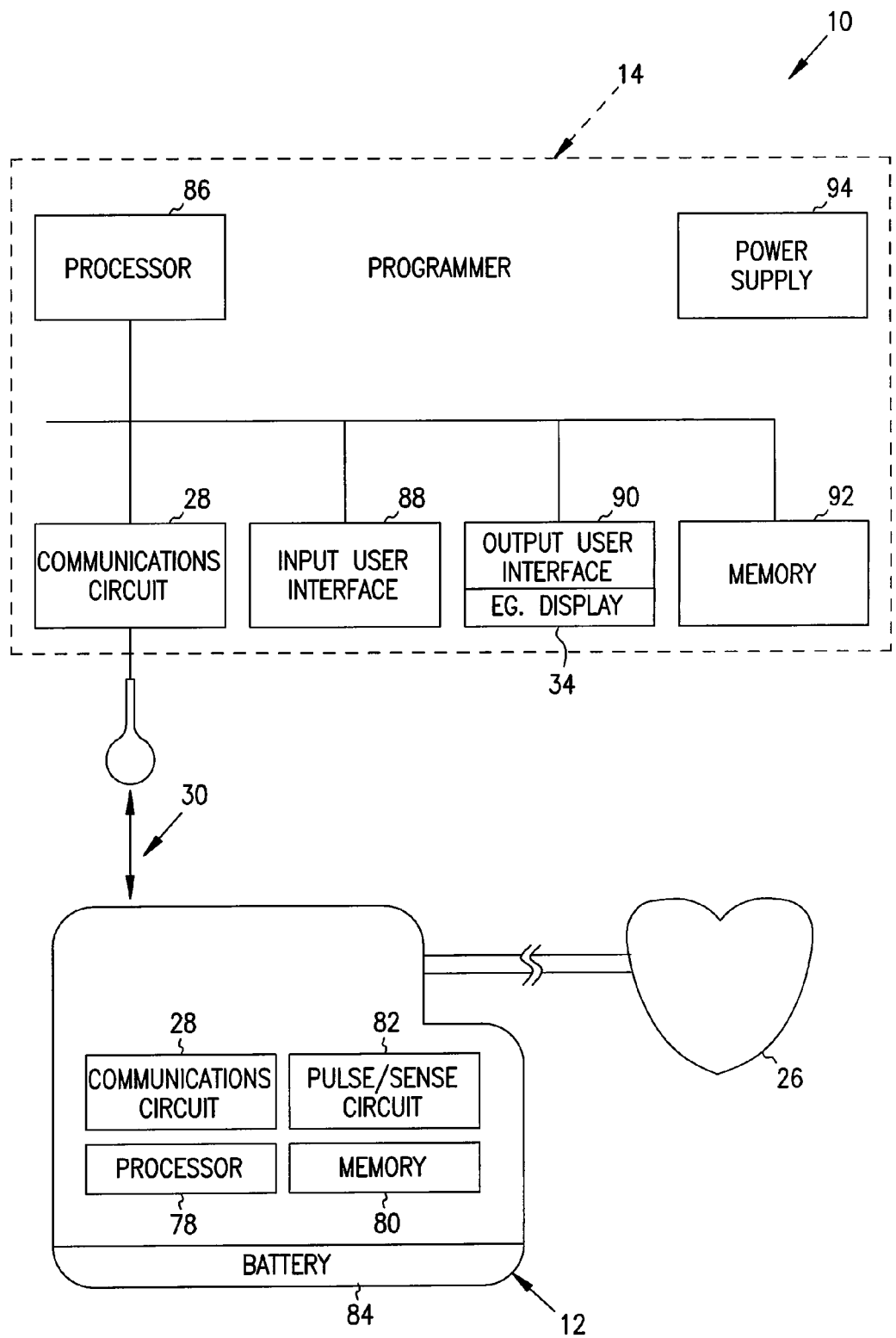
FIG. 2 is a block diagram of one embodiment of the system of FIG. 1.

FIGS. 1 and 2 show the programmer 14 coupled or otherwise in communication with the medical device 12. In one embodiment, the programmer 14 is coupled through complementary telemetry circuits 28 that provide a radio frequency telemetry channel 30 between the programmer 14 and the device 12. The medical device 12 has programmable parameters that are adjusted in an attempt to optimize the medical device 12 for a particular patient, and the programmer 14 is used to change or program these parameters. Also, as discussed above, the medical device 12 collects cardiac event data, such as paced cardiac events and sensed intrinsic cardiac events, and stores it in memory 80. This data is transferred from the medical device 12, through the communication channel 30, and to the programmer 14, which has means for retrieving and displaying the data regarding these cardiac events. The programmer 14 retrieves the data regarding the cardiac events at these cardiac sites, and provides a graph 32 of these cardiac events.

In one embodiment, the graph 32 is, or is formed on, an electronic screen display 34 such as a CRT monitor or a liquid crystal display LCD, for example, that forms an integral part of the programmer 14. In other embodiments, the display 34 includes other means for displaying the graph 32 of cardiac events, including but not limited to, printing out the graph 32 on a printer, and projecting the graph 32 of cardiac events on a device in communication with the programmer 14 such as, for example, a local peripheral device, a remote device, or a device networked to the programmer 14. Thus, the graph 32 may be produced as both a printed and projected image.

As discussed earlier, in addition to its ability to pace and sense cardiac events, the medical device 12 provides means for collecting data regarding cardiac events that occurred at various cardiac sites where an electrode 24 is located, and collects or records data regarding these cardiac events in a memory 80. This data includes sensed intrinsic cardiac events such as sensed P waves and sensed R waves and/or paced cardiac events that have been induced by the medical device 12. These cardiac events are then able to be displayed by the programmer 14, which has means for retrieving data and further has means for representing the cardiac events occurring at these sites in a graph 32 on a display 34. In one embodiment, these means for retrieving data and means for representing the cardiac events are provided by hardware and programming.

Figure 3:
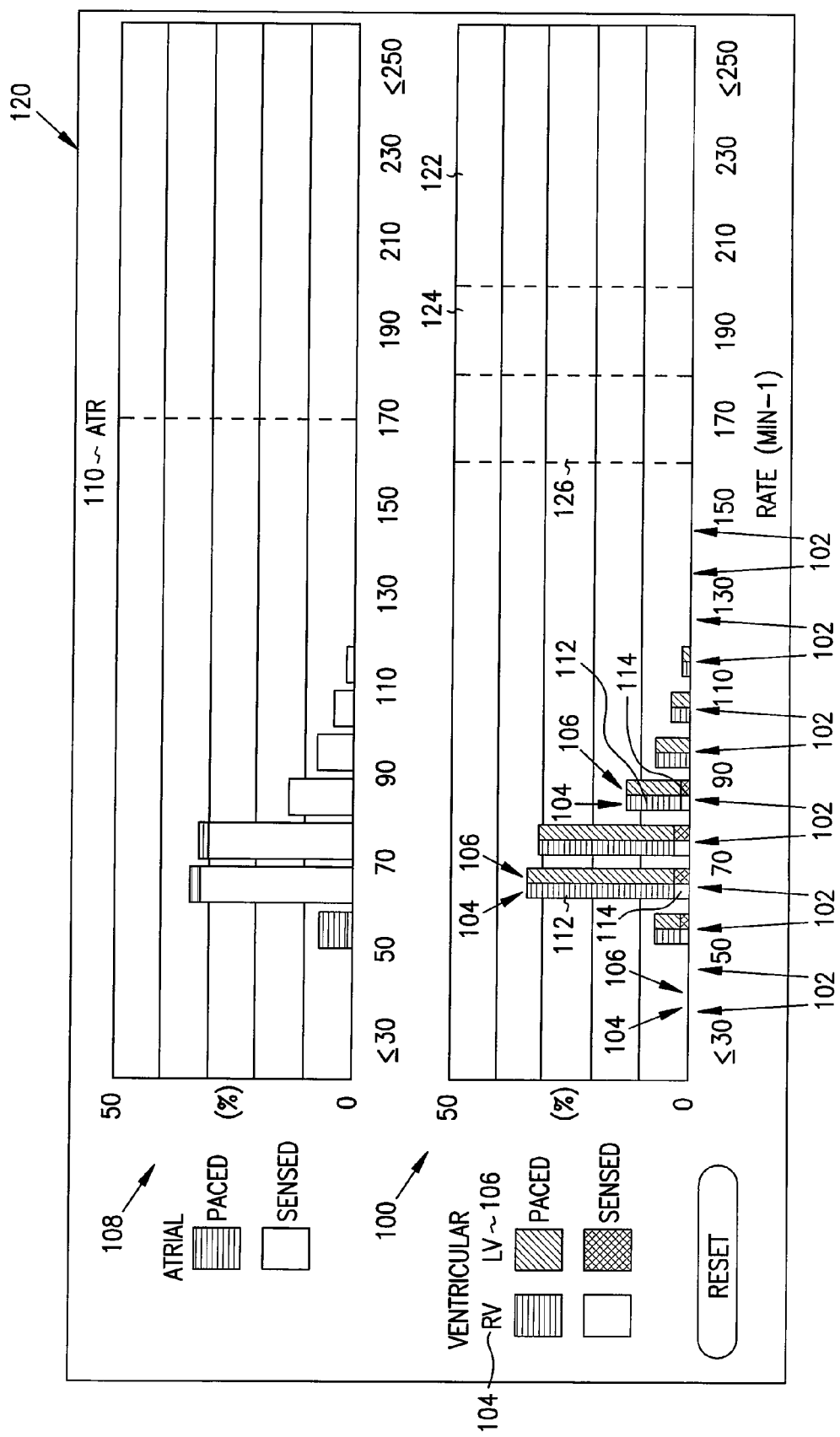
FIG. 3 is a first example of a cardiac event graph in which a first and second cardiac event distributions are adjacent to each other in a histogram bin.
Figure 4:
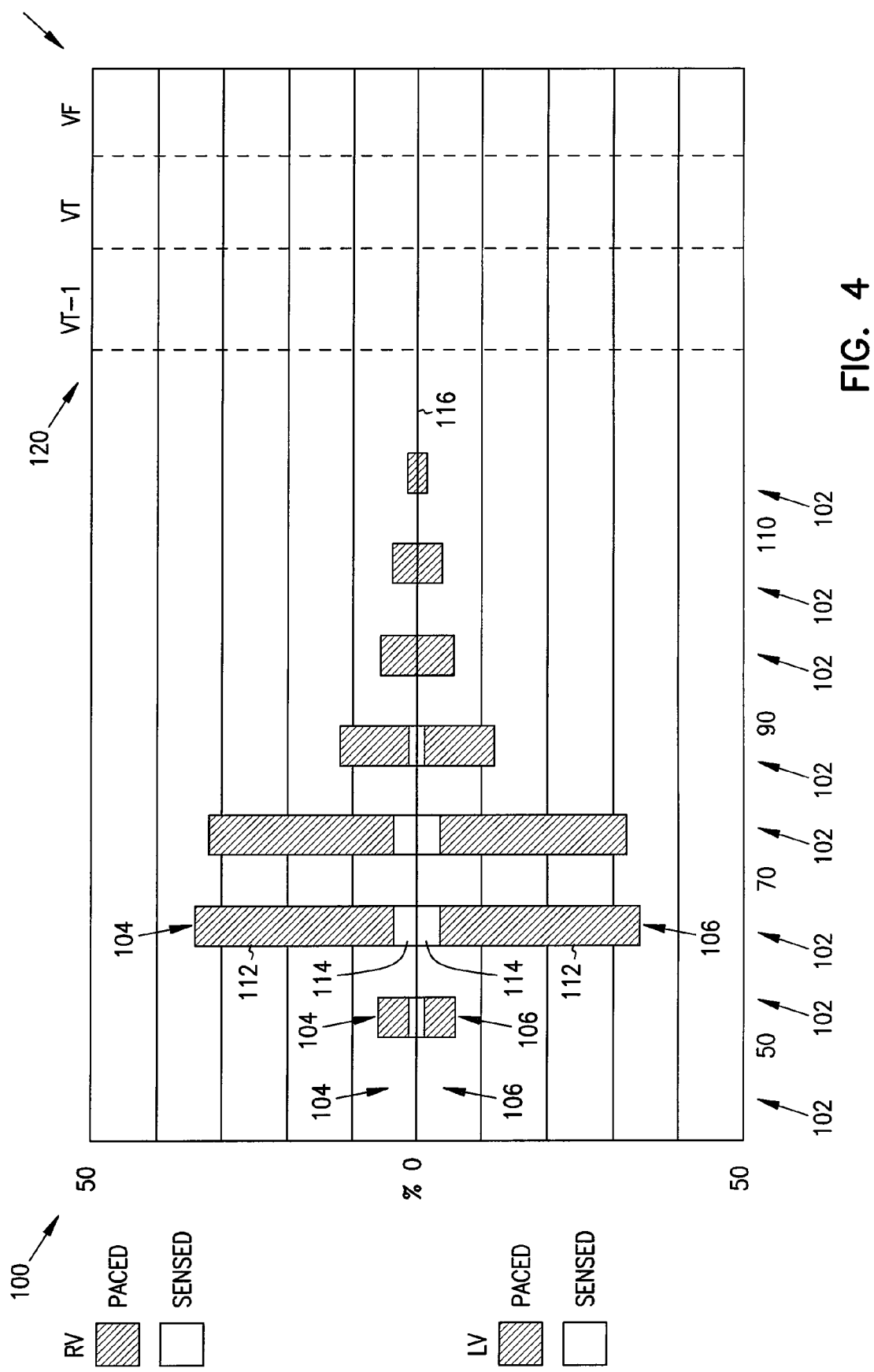
FIG. 4 is a second example of a cardiac event graph in which a first and second cardiac distributions are on opposing sides of a histogram axis.

In one embodiment, as generally illustrated in FIGS. 3 and 4, the graph 32 is a histogram 100 that generally comprises a plurality of histogram bins 102 that provide a statistical distribution of the cardiac events for these sites. Each histogram bin 102 includes a first cardiac event distribution 104 for cardiac events that occurred at a first cardiac site, and a second cardiac event distribution 106 for cardiac events that occurred at a second cardiac site. The ventricular histogram has bins 102 that represent cardiac events that occur at a particular rate. For example, the illustrated histogram has bins 102 that represent cardiac events within ten beats per minute intervals (i.e. "30-39" beats per minute, "40-49" beats per minute, and up to "240-249" beats per minute). The increment used to define the histogram bins 102 may vary as desired for an application.

In the embodiment illustrated in FIG. 3, the first cardiac event distribution 104 is adjacent to the second cardiac event distribution 106. Referring to the "60-69" bin, the second cardiac event distribution 106 is provided adjacent to the first cardiac event distribution 104. In this illustrated embodiment, the first cardiac event distribution 104 represents right ventricular cardiac events, and the second cardiac event distribution 106 represents left ventricular cardiac events. Other embodiments display other cardiac event distributions for other cardiac sites. And as illustrated in the embodiment shown in FIG. 3, the programmer 14 further provides a second histogram, i.e. atrial histogram 108, to represent atrial events. This second histogram 108 shows the paced and sensed atrial cardiac events, and further displays a programmed atrial trigger rate (ATR) 110. The second histogram 108 supplements the first histogram 100 that provides a graph of the cardiac event data as two or more statistical distributions for the two or more cardiac sites. As will be discussed below with respect to FIGS. 6 through 11, the second histogram 108 along with the first histogram 100 provides a way in which a clinician can compare ventricular cardiac events against atrial cardiac events.

Additionally, in one embodiment, a color scheme is used to distinguish the various distributions in the graph 32. Color schemes include the use of colors that display well on color monitors or printers, or gray tones for black and white monitors and printers. In the illustrated example of FIG. 3, the sensed event in the right ventricle is darker than the sensed event in the left ventricle. Additionally, the distributions are further distinguishable using different fillings. In the illustrated example of FIG. 3, a same color is used to display the paced events 112 and sensed events 114 for the right ventricle. Additionally, a same color is used to display paced events 112 and sensed events 114 for the left ventricle. The color used for the left ventricle is different than the color used for the right ventricle. The paced events 112 and the sensed events 114 are distinguished by using a hatched filling for the paced events 112 and a solid filling for the sensed events 114. Although the exact color scheme or fill scheme used may vary, these schemes enhance the ability of the graph 32 to quickly and easily convey or represent the cardiac events in a meaningful way for viewing and comparison.

In another embodiment illustrated in FIG. 4, the histogram 100 further comprises a histogram axis 116 extending through each of the histogram bins. In this embodiment, each histogram bin 102 includes a first cardiac event distribution 104 and a second cardiac event distribution 106, with the first cardiac event distribution 104 and the second cardiac event distribution 106 on opposing sides of the histogram axis 116.

Both the embodiment illustrated in FIG. 3 and the embodiment illustrated in FIG. 4 provide a histogram 100 that allows a user to view and compare cardiac events at two or more sites in a meaningful manner as frequency distributions.

FIG. 2 illustrates a block diagram of the system 10 shown in FIG. 1. In one embodiment, the medical device 12 is a programmable microprocessor-based system that generally comprises a processor 78, a memory 80, a telemetry circuit 28, pulse/sense circuitry 82, and a power supply or battery 84. The processor 78 and memory 80 are used to control the process steps conducted by the medical device 12. For example, the processor 78 is programmed to detect a sensed condition or response in a patient's heart 26 and to respond appropriately. The memory 80 contains parameters for various pacing and sensing modes, and further stores data concerning the condition of the heart 26 as derived from the received cardiac signals. In one embodiment, this stored data includes data regarding paced and sensed cardiac events. The medical device 12 uses the pulse/sense circuitry 82 to interface with the lead electrodes 24, i.e. to transmit the signal to the heart 26 and to receive the signal from the heart 26 through these electrodes 24. The telemetry circuit 28 enables the medical device 12 and the programmer 14 to communicate with each other.

The illustrated programmer device 14 provides another aspect of the present subject matter. The programmer 14 generally comprises a processor 86, a circuit 28 for communicating with a medical device 12, an input user interface 88, an output user interface 90, memory 92 and a power supply 94. In one embodiment, the circuit for communicating with a medical device comprises telemetry circuitry 28. As discussed earlier, the medical device 12 is capable of collecting or acquiring data for both sensed and paced cardiac events occurring at two or more cardiac sites. This data is transferred, retrieved or otherwise acquired by the programmer 14 through the communication circuitry 28.

In one embodiment, the input user interface 88 includes, but is not limited to, a keyboard 96, a mouse 98, a light pen and a touch screen. Further, the output user interface 90 includes, but is not limited to, printers and displays. In one embodiment, the graph 32 is, or is formed by, an electronic screen display 34 such as a CRT monitor or LCD, for example, that forms an integral part of the programmer 14. In other embodiments, the display 34 includes other means for displaying cardiac events, including but not limited to, printing or projecting the graph 32 of the cardiac events on a device in communication with the programmer 14 such as, for example, a local peripheral device, a remote device, or a device networked to the programmer 14. Thus, the graph 32 may be produces as both a printed and a projected image.

Thus, according to this aspect, the programmer device 14 generally comprises circuitry 28 for communicating with a medical device 12, and a display 34 upon which the graph 32 is produced. The circuitry 28 provides means for communicating with a cardiac stimulation device or medical device 12 that is adapted for collecting data regarding cardiac events occurring at two or more cardiac sites.

The medical device 12 distributes electrodes 24 to the heart 26 to provide cardiac sites from which cardiac events are collected. In one variation, the medical device 12 distributes two or more electrodes 24 into one chamber of the heart. In another variation the medical device 12 distributes at least one electrode 24 into two or more chambers. In yet another variation the medical device 12 distributes two or more electrodes 24 into one chamber and at least one electrode 24 into two or more chambers of the heart. As discussed above, these electrodes 24 are configured to either pace a cardiac event or to sense an intrinsic cardiac event, and the display 32 represents the cardiac events that occurred at the two or more sites where electrodes 24 are positioned. In one embodiment, the data collected by the medical device 12 and displayed include both paced cardiac events 112 and sensed intrinsic cardiac events 114. And since the medical device 12 is able to distribute the electrodes 24 in a number of ways, the two or more sites from which the cardiac event data are collected and displayed include: a first site in a first cardiac chamber and a second site in a second cardiac chamber; a first site and a second site in a first cardiac chamber; and a first site and a second site in a first cardiac chamber and a third site in a second cardiac chamber. These illustrated variations are not exhaustive or exclusive, but rather illustrate that multiple cardiac sites from which the cardiac events are collected and displayed may be distributed in one and/or among two or more chambers of a heart. Appropriate hardware and programming provide means for retrieving the data, and means for representing the cardiac events occurring at the cardiac sites in a display 32.

The graph 32 already has been discussed above with respect to the system aspect 10, and now is generally discussed here with respect to the programmer device 14. In one embodiment of the programmer device 14, the graph 32 is a histogram 100. The histogram 100 comprises a plurality of histogram bins 102 that provide frequency distribution(s) for representing cardiac events. Each histogram bin includes a first and a second cardiac event distribution 104 and 106. The first cardiac event distribution 104 represents cardiac events that occurred at a first cardiac site, and the second cardiac event distribution 106 represents cardiac events that occurred at a second cardiac site. In one embodiment, the first cardiac event distribution 104 is adjacent to the second cardiac event distribution 106. In an alternative embodiment, the histogram 100 farther comprises a histogram axis 116 extending through each of the histogram bins 102. The first cardiac event distribution 104 and the second cardiac event distribution 106 are on opposing sides of this axis 116.

According to one embodiment, the first cardiac event distribution 104 and the second cardiac event distribution 106 each include both paced cardiac events, i.e. a paced cardiac event distribution 112, and sensed intrinsic cardiac events, i.e. a sensed cardiac event distribution 114. Within this embodiment, the first cardiac event distribution 104 and the second cardiac event distribution 106 are formed by a summation of the paced cardiac event distribution 112 and the sensed cardiac event distribution 114. According to one embodiment as illustrated in FIG. 3, the first cardiac event distributions 104 and the second cardiac event distributions 106 are distinguished using different colors, and the distributions associated with the paced cardiac events 112 and the sensed intrinsic cardiac events 114 are distinguished using different fillings. In the specific embodiment illustrated in FIG. 3, the histogram 100 represents both a right ventricular cardiac event distribution 104 and a left ventricular cardiac event distribution 106, and further includes a second histogram 108 to represent atrial events.

Another aspect provides a histogram 100 for providing a statistical distribution of the cardiac event data for the two or more sites. The graph 32 has already been discussed above with respect to the system aspect 10 and programmer device 14 aspect, and now is discussed here with respect to the histogram display aspect 100. The histogram display 100 generally comprises or provides a plurality of histogram bins 102 that represent cardiac events. Each of the histogram bins 102 include a first cardiac event distribution 104 or a portion thereof and a second cardiac event distribution 106 or a portion thereof. The first cardiac event distribution 104 represents cardiac events that occurred at a first cardiac site, and the second cardiac event distribution 106 represents cardiac events that occurred at a second cardiac site. Even if no cardiac events occurred in a bin 102, there still is a cardiac event distribution, or representation of the cardiac event, for that bin because it represents that no event occurred with respect to that bin. For example, in the "40-49" rate bin of FIG. 3, the first cardiac event distribution 104 and the second cardiac event distribution 106 are zero.

In one embodiment of the histogram, as generally illustrated in FIG. 3, the first cardiac event distribution 104 is adjacent to the second cardiac event distribution 106 in each of the histogram bins 102, i.e. portions or representations of the distributions are provided adjacent to each other in each bin. For example, the "60-69" bin 102 of FIG. 3 contains both the first cardiac event distribution 104 and the second cardiac event distribution 106 side-by-side. In an alternative embodiment, as generally illustrated in FIG. 4, a histogram axis 116 extends through each of the histogram bins 102, and the first cardiac event distribution 104 and the second cardiac event distribution 106 are on opposing sides of the histogram axis 116.

Because of the variety of ways in which the electrodes 24 of the medical device 12 can be arranged in a heart 26, there are a variety of combinations of cardiac sites from which cardiac event data is collected. In one variation, the first cardiac site is in a first cardiac chamber and the second site is in a second cardiac chamber. One embodiment of this variation is reflected in the histogram 100 of FIG. 3, in which the first cardiac event distribution 104 is a right ventricle 44 distribution and the second cardiac event distribution 106 is a left ventricle 52 distribution. In another variation, the first cardiac site and the second cardiac site are in a first cardiac chamber. In yet another variation, there is a third cardiac event distribution for cardiac events at a third site. The first site and the second site are in a first cardiac chamber, and the third site is in a second cardiac chamber. These variations are provided as examples, and not as an exclusive list.

In one embodiment the first cardiac event distribution 104 and the second cardiac event distribution 106 each include both paced cardiac events 112 and sensed intrinsic cardiac events 114. In one embodiment of the histogram 100, the first and second event distributions 104 and 106 are distinguished using different colors, and the distributions for the paced cardiac events 112 and the sensed intrinsic cardiac events 114 are distinguished using different fillings.

In one embodiment as illustrated in FIG. 3, the graph 32 includes tachy zone rate thresholds 120. The medical device 12 provides a particular therapy for the ventricular tachycardia, i.e. VT, a condition of the patient that is represented by these zones. Tachycardia is cardiac arrhythmia characterized by a rapid rate. This rapid rate may be normal as if induced by exercise, or may indicate a pathology. These tachy zone rate thresholds 120 are programmed boundaries that define zones or stages for a particular patient's condition for which a defibrillator, for example, applies either specially timed shocks or pulses or a high voltage shock to the heart muscle to interrupt or disrupt the fast rhythm. In the illustration of FIG. 3, these zones include a ventricular fibrillation zone (VF) 122, a ventricular tachycardia zone (VT) 124, and a pre ventricular tachycardia zone (VT-1) 126. These zone rate thresholds 120 assist a user with evaluating therapy.

In one embodiment, the histogram 100 may be projected on an electronic display or screen display 34 such as a CRT monitor or LCD. In another embodiment, the histogram 100 is printed on a printer. In one embodiment, the histogram 100 is provided by the programmer device 14 to an integral monitor or printer, a local peripheral, a networked resource, or a remote resource. In another embodiment, another device such as a stand-alone display device separate from the programmer 14 provides the histogram 100. This stand-alone display device has means for retrieving the data regarding the cardiac events occurring at the cardiac sites, and further has means for providing a graph 32 representing these cardiac events.

Figure 5:
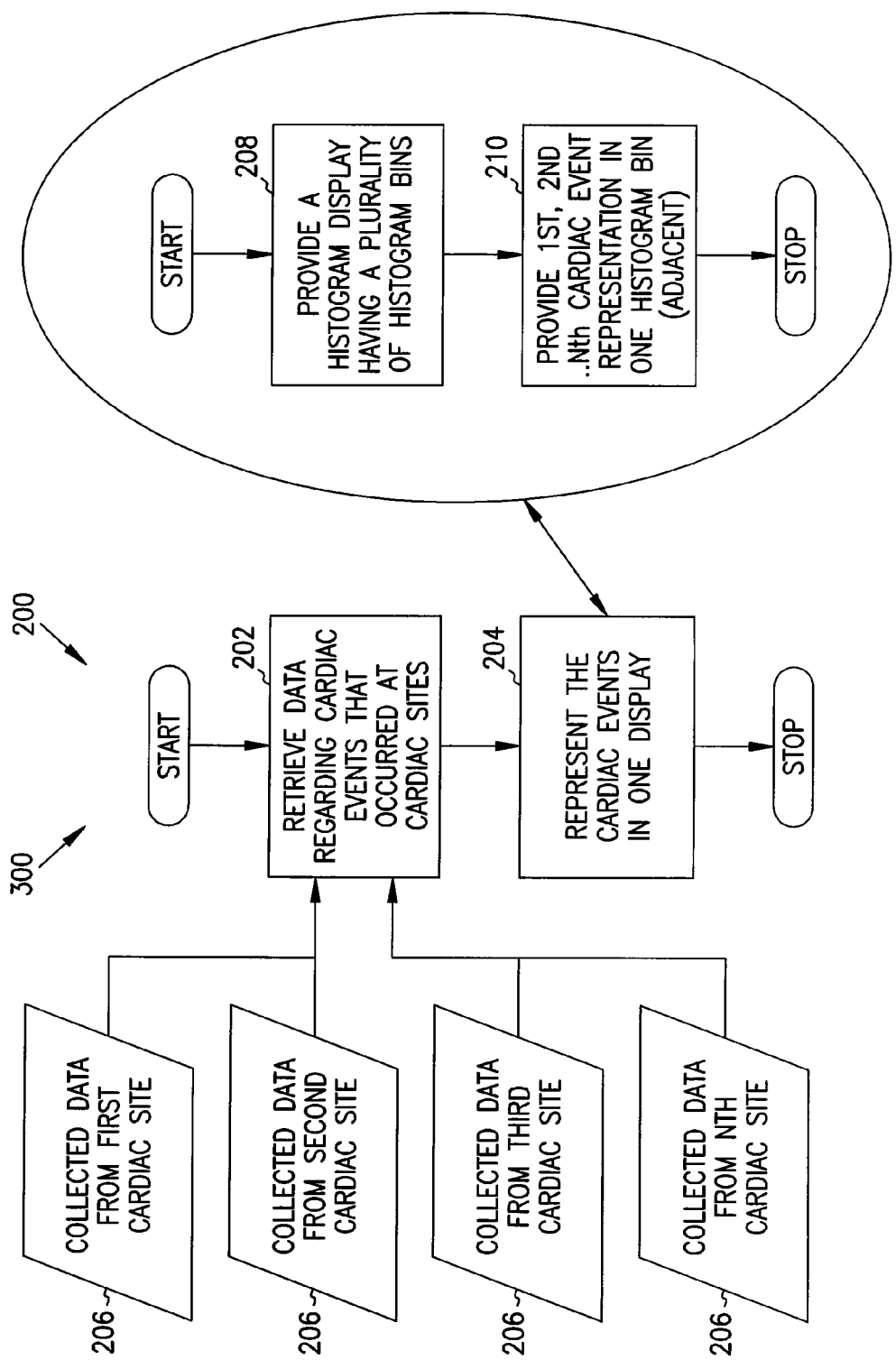
FIG. 5 is a flow diagram representing method and software program aspects.

Another aspect provides a software program 200 that provides a programming interface for an implantable medical device 12. FIG. 5 illustrates a flow chart for the software program 200. The software program 200 is encoded in a computer-readable medium, i.e. the memory 92 of the programmer 14 for example. The illustrated software program 200 generally executes the following: at 202, retrieving data regarding cardiac events occurring at two or more sites; and at 204, representing the cardiac events occurring at the two or more sites in a graph 32. Receiving data regarding cardiac events requires a collected data input 206 for the sites. As illustrated, this collected data is from the first and second cardiac sites. The present subject matter is not limited to two cardiac sites. The illustration shows that data may be taken from a third site or even additional sites, i.e. an Nth site. In one embodiment, this data is collected by the medical device 12 and is stored in the memory 80 of the medical device 12.

The graph 32 generated by the software program 200 generally comprises a plurality of histogram bins 102 that represent cardiac events. Each histogram bin 102 includes a first cardiac event distribution 104 for cardiac events that occurred at a first cardiac site, and a second cardiac event distribution 106 for cardiac events that occurred at a second cardiac site. In one embodiment, the first cardiac event distribution 104 is adjacent to the second cardiac event distribution 106. Therefore, in one embodiment, representing the cardiac events in one display generally comprises: at 208, providing a histogram distribution 100 having a plurality of histogram bins 102; and at 210, providing a 1st, 2nd and even up to an Nth cardiac event distribution, or a portion or representation thereof, in one histogram bin 102.

Because of the variety of ways in which the electrodes 24 of the medical device 12 can be arranged in or proximate to a heart 26, there are a variety of combinations of cardiac sites from which cardiac event data is collected. In one variation, the first site is in a first cardiac chamber and the second site is in a second cardiac chamber. In one embodiment that represents this variation, the first cardiac event distribution 104 is a right ventricle 44 cardiac event distribution and the second cardiac event distribution 106 is a left ventricle 52 cardiac event distribution. In another variation, the graph 32 further comprises a third cardiac event distribution for cardiac events at a third site. The first site and the second site are in a first cardiac chamber, and the third site is in a second cardiac chamber. This third cardiac event distribution forms a third column adjacent to the first and second cardiac event distributions 104 and 106, or portions thereof, in the bins.

Additional features of the display 32 have been discussed above with respect to the system 10, programming device 12 and histogram display 100 aspects of the present subject matter.

Another aspect, also as generally illustrated in FIG. 5, provides a method 300 that generally comprises: at 202, retrieving data regarding cardiac events occurring at two or more sites; and at 204, representing the cardiac events occurring at the two or more sites in a graph 32.

In one embodiment, representing the cardiac events comprises: at 208, providing a histogram 100 having a plurality of histogram bins 102 representing cardiac events; and at 210, providing a first cardiac event distribution 104 and a second cardiac event distribution 106 in one of the histogram bins 102. The first cardiac event distribution 104 represents cardiac events that occurred at a first site and the second cardiac event distribution 106 represents cardiac events that occurred at a second site.

In one embodiment, providing at 208 a first cardiac event distribution 104 and a second cardiac event distribution 106 in one of the histogram bins 102 comprises providing the first cardiac event distribution 104 adjacent to the second cardiac event distribution 106. In an alternative embodiment, providing at 208 a first cardiac event distribution 104 and a second cardiac event distribution 106 in one of the histogram bins 102 comprises providing a histogram axis 116, and providing the first cardiac event distribution 104 and the second cardiac event distribution 106 on opposing sides of the histogram axis 116.

Because of the variety of ways in which the electrodes of the medical device 12 can be arranged in or proximate to a heart 26, there are a number of variations with respect to the cardiac sites. In one variation, the first cardiac site is in a first cardiac chamber and the second cardiac site is in a second cardiac chamber. In one embodiment that represents this variation, the first cardiac event distribution 104 is a right ventricle 44 distribution and the second cardiac event distribution 106 is a left ventricle 52 distribution.

In one embodiment, providing a first cardiac event distribution 104 and a second cardiac event distribution 106 in one of the histogram bins 102 comprises providing a first cardiac event distribution 104, a second cardiac event distribution 106 and a third cardiac event distribution in one of the histogram bins. The third cardiac event distribution is represented as a third column in the histogram bin 102, and represents cardiac events that occurred at a third cardiac site. In this embodiment, the first cardiac site and the second cardiac site are in a first cardiac chamber, and the third cardiac site is in a second cardiac chamber.

Additional features of the graph 32 have been discussed above with respect to the system aspect of the present invention.

Figure 6:
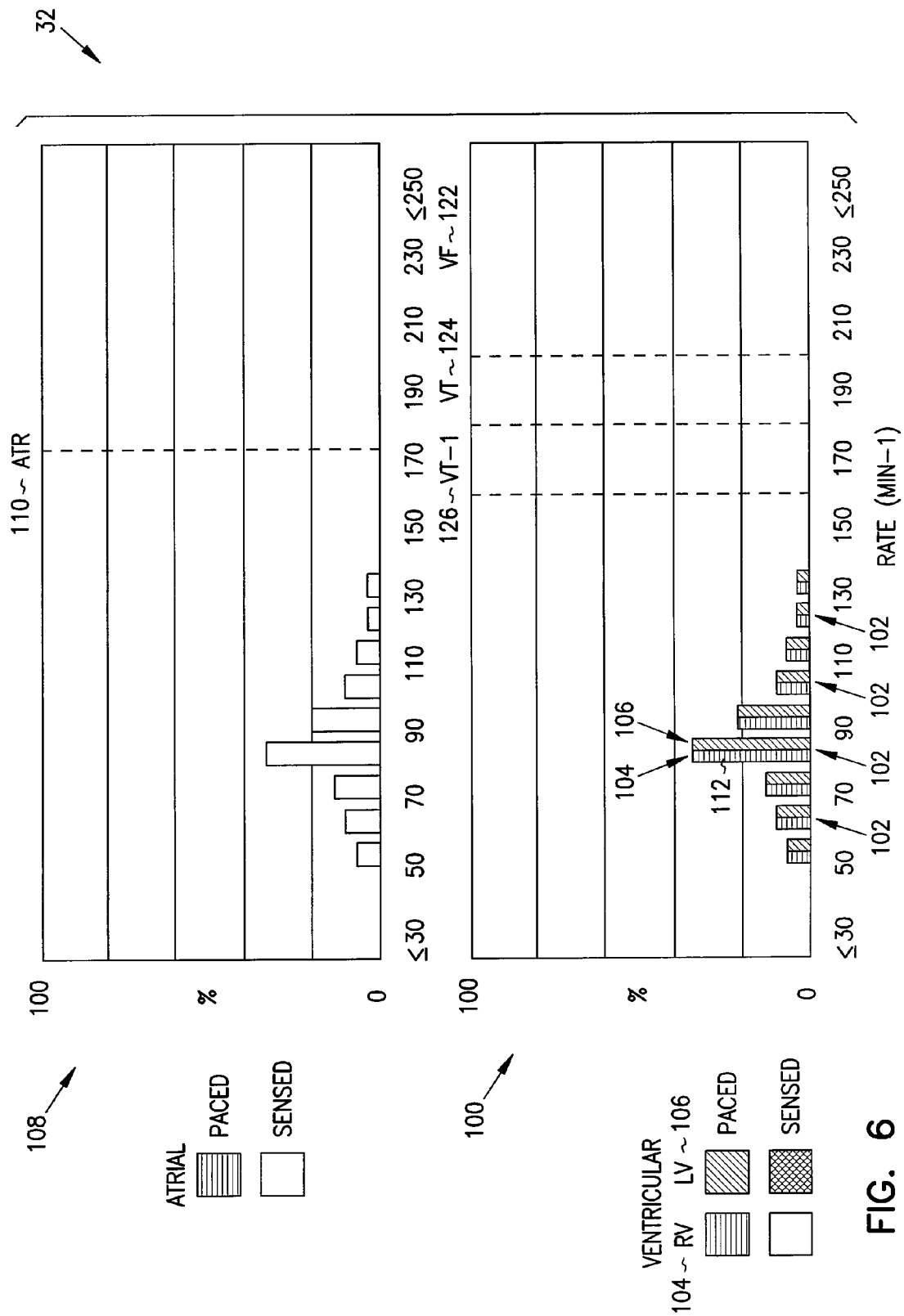
FIG. 6 is an example of the cardiac event graph illustrating a desired therapy in which atrial tracking results in BV pacing.
Figure 7:
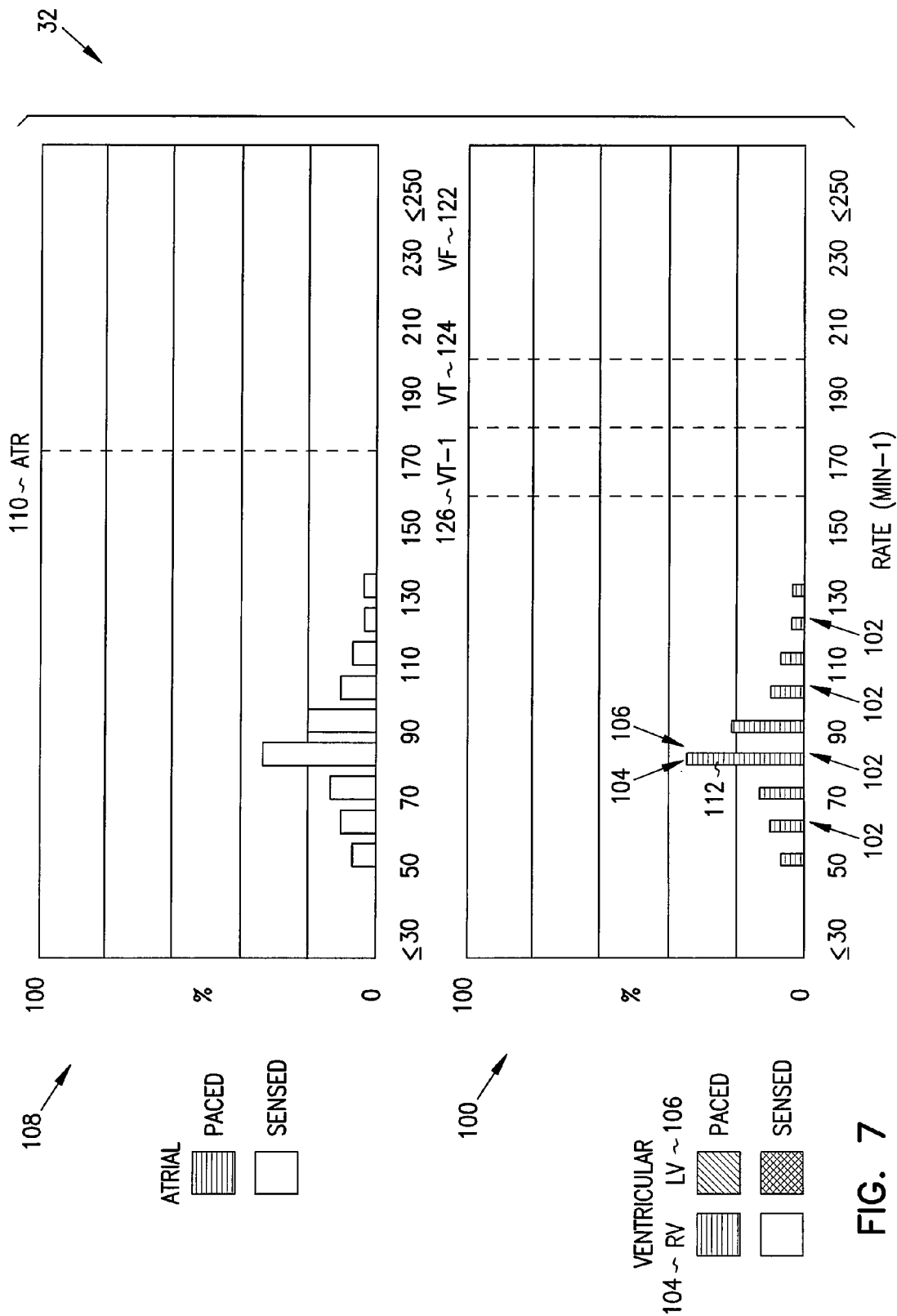
FIG. 7 is an example of the cardiac event graph illustrating a desired therapy in which atrial tracking results in RV pacing.
Figure 8:
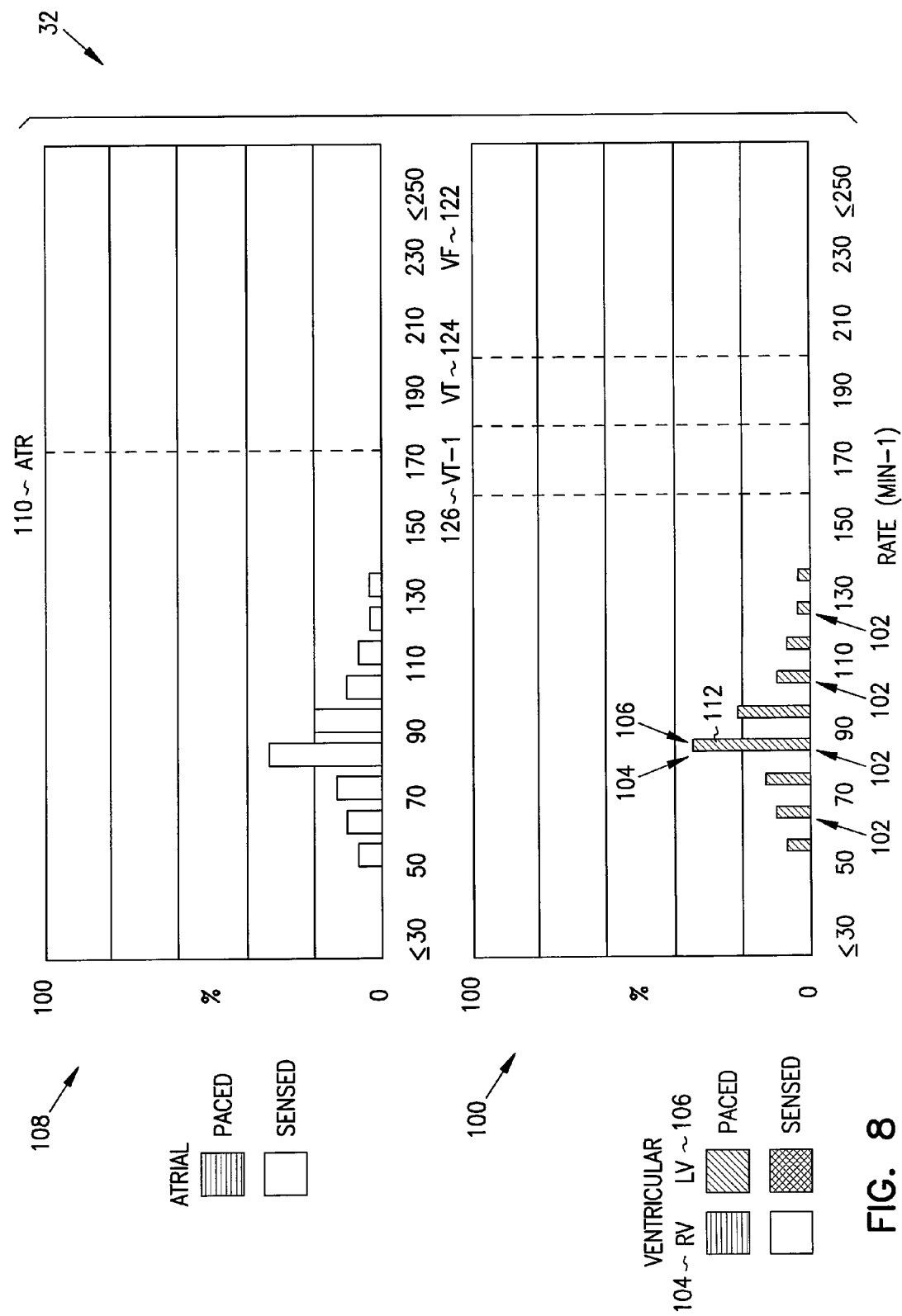
FIG. 8 is an example of the cardiac event graph illustrating a desired therapy in which atrial tracking results in LV pacing.
Figure 9:
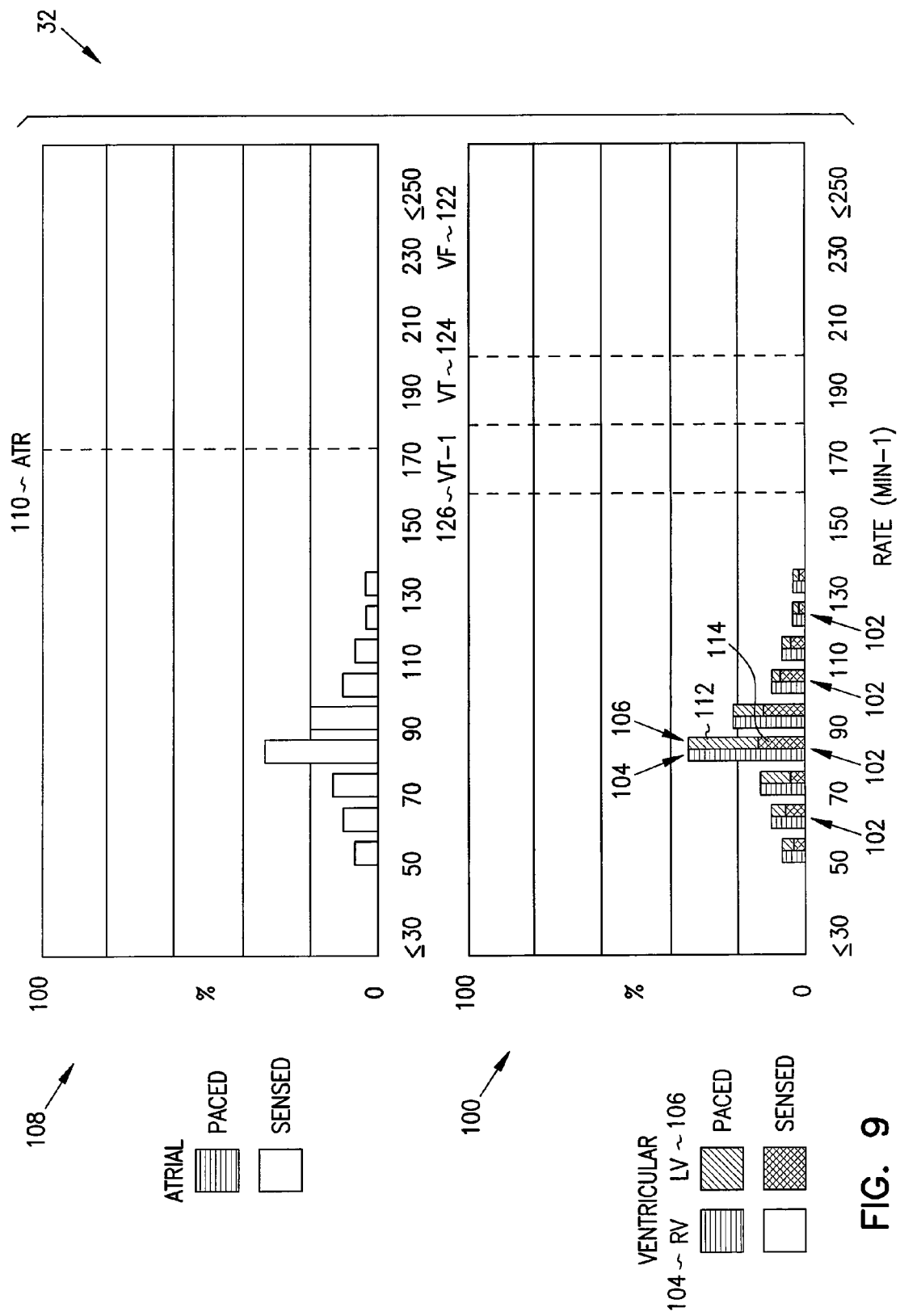
FIG. 9 is an example of the cardiac event graph illustrating a compromised therapy in which there is significantly reduced LV pacing due to LV oversensing.
Figure 10:
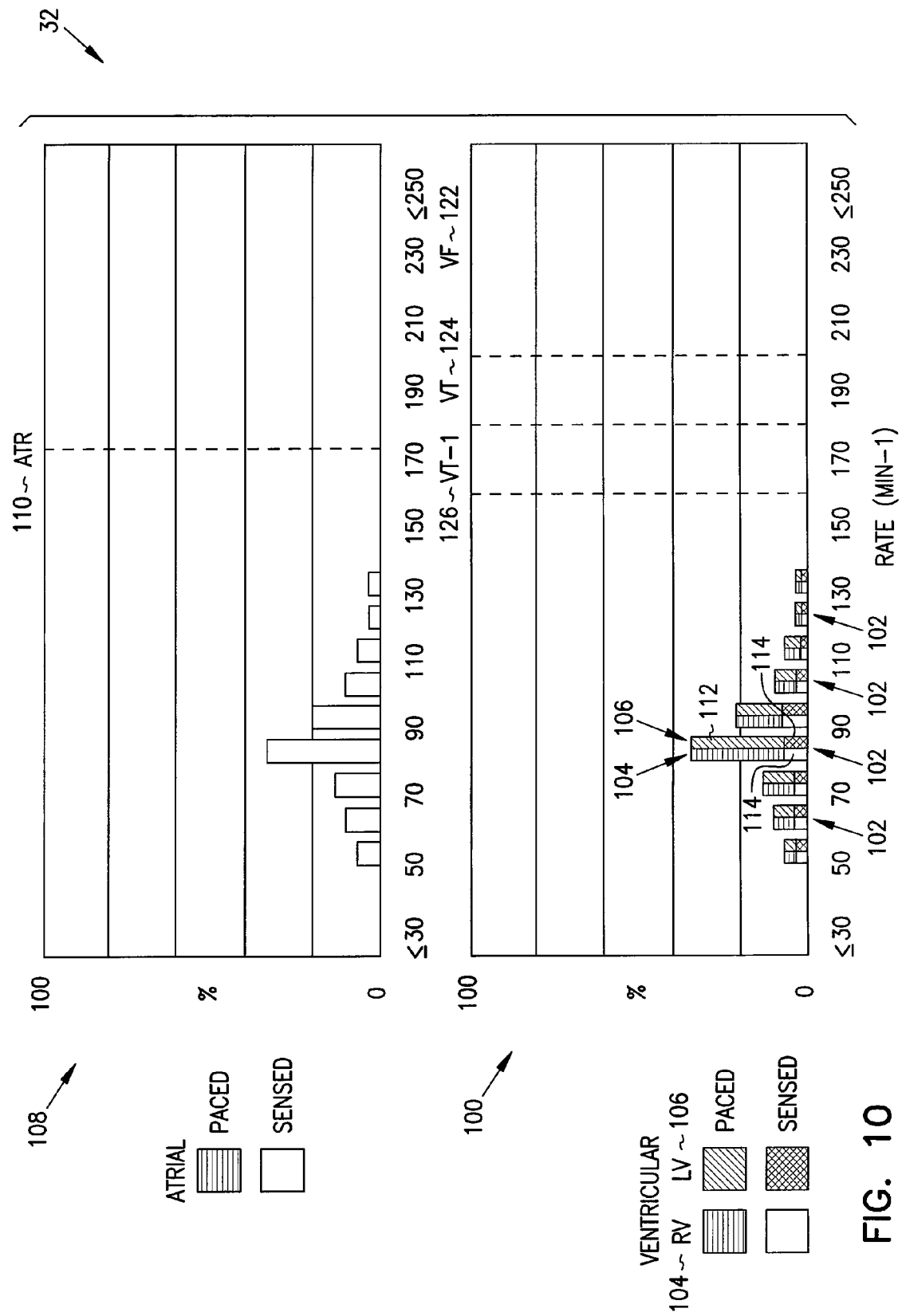
FIG. 10 is an example of the cardiac event graph illustrating a compromised therapy in which there is reduced BV pacing due to the PR interval being smaller than the AV delay independent of rate.
Figure 11:
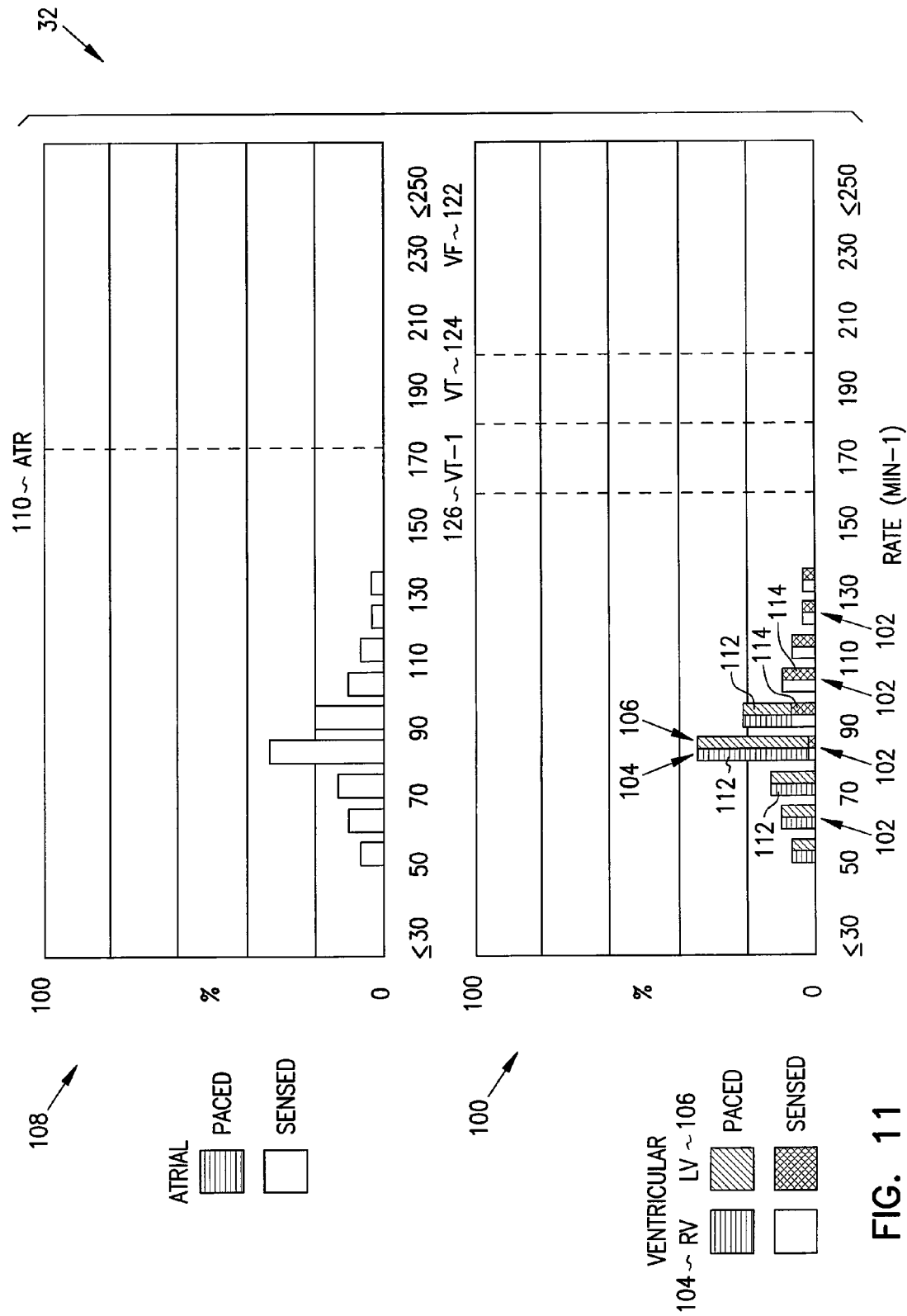
FIG. 11 is an example of the cardiac event graph illustrating a compromised therapy in which there is reduced BV pacing due to the PR interval being smaller than the AV delay at elevated rates.

FIGS. 6 through 11 provide examples of how the cardiac event display is used to provide the clinician with diagnostics that reveal loss of therapy. The examples provided herein are nonexclusive. FIGS. 6, 7 and 8 provide examples of the cardiac event display illustrating a desired therapy, and FIGS. 9, 10 and 11 provide examples of the cardiac event display illustrating a compromised therapy.

FIG. 6 provides an example of the cardiac event graph 32 illustrating a desired therapy in which atrial tracking results in BV pacing. The histogram 100 illustrates BV therapy, i.e. pacing in both the right and left ventricles as illustrated by the first and second cardiac event distributions 104 and 106, being delivered across all occurring atrial rates as illustrated by the atrial histogram 108. The illustrated paced RV and LV events are the desired therapy when the device is programmed to deliver BV therapy.

FIG. 7 provides an example of the cardiac event graph 32 illustrating a desired therapy in which atrial tracking results in RV pacing. The histogram 100 illustrates RV therapy, i.e. pacing in the right ventricle as illustrated by the first cardiac event distribution 104, being delivered across all occurring atrial rates as illustrated by the atrial histogram display 108. The illustrated paced RV events are the desired therapy when the device is programmed to deliver RV therapy.

FIG. 8 provides an example of the cardiac event graph 32 illustrating a desired therapy in which atrial tracking results in LV pacing. The histogram 100 illustrates LV therapy, i.e. pacing in the left ventricle as illustrated by the second cardiac event distribution 106, being delivered across all occurring atrial rates as illustrated by the atrial histogram 108. The illustrated paced LV events are the desired therapy when the device is programmed to deliver LV therapy.

FIG. 9 provides an example of the cardiac event graph 32 illustrating a compromised therapy in which there is significantly reduced LV pacing due to LV oversensing. The histogram 100 illustrates the compromise in therapy due to LV (left ventricle) sensing occurring before the ventricular escape interval. The ventricular escape interval is the period between a ventricular sensed event and the next ventricular output pace. In medical devices that use only RV (right ventricle) sensing to reset the ventricular escape time, these LV senses will inhibit LV pacing but not RV pacing. Therefore, the loss of LV pacing, but not RV pacing, as illustrated by the sensed event 114 in the left ventricle cardiac event distribution 106 in this histogram 100 represents LV oversensing and has significant diagnostic value to the clinician. The clinician may be able to mitigate this loss of therapy by reprogramming the sensing characteristics of the LV channel, such as sensing level, refractory time, and blanking time.

FIG. 10 provides an example of the cardiac event graph 32 illustrating a compromised therapy in which there is reduced BV pacing due to the PR interval being smaller than the AV delay independent of rate. The histogram 100 illustrates the compromise in therapy due to sensing the RV, i.e. the sensed event 114 in the right ventricle cardiac event distribution 104, some of the time across all atrial rates as illustrated by the atrial histogram 108. This illustrates what would occur in a patient when the PR interval is shorter than the programmed AV delay much of the time and is not dependent on rate. The PR interval is the period between an atrial sensed event (P) and a ventricular sensed event (R), and the AV delay is the period between an atrial sensed or paced event and the delivery of a ventricular pace pulse. The clinician may be able to mitigate this loss of therapy by reprogramming the fixed AV delay to a shorter period.

FIG. 11 provides an example of the cardiac event graph 32 illustrating a compromised therapy in which there is reduced BV pacing due to the PR interval being smaller than the AV delay at elevated rates. The histogram 100 illustrates the compromise in therapy due to sensing the RV at elevated atrial rates. This illustrates what would occur in a patient when the PR interval decreases with increasing rate and eventually gets shorter than the programmed AV delay. The clinician may able to mitigate this loss of therapy by reprogramming the AV delay from fixed to dynamic or more aggressively reprogramming the AV delay if it is already enabled.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL). A ventricular escape interval can also be triggered by an atrial sense in an atrial tracking mode.

In ventricular resynchronization therapy, one or both ventricles are paced in an attempt to improve the coordination of ventricular contractions. In a ventricular resynchronization pacing mode, pacing stimulation is applied to one or both ventricles in a manner that improves the coordination of ventricular contractions and thereby improve ventricular pumping efficiency.

In delivering such therapy, for example, it may be useful to pace only one ventricle on an inhibited demand basis in accordance with sense signals received from the opposite ventricle, pace one ventricle in a triggered mode in which an intrinsic beat in one ventricle triggers a pace in the opposite ventricle, pace both ventricles on an inhibited demand basis in accordance with sense signals received from only one ventricle, or pace both ventricles in a combination of triggered and inhibited demand modes. In the examples of resynchronization therapy that follow, the ventricular pacing modes are based upon intrinsic activity in the right ventricle. It should be appreciated, however, that equivalent embodiments could be applied to pacing modes based upon left ventricular intrinsic activity.

One implementation of resynchronization therapy is biventricular (BV) pacing. In BV pacing, a left ventricular pace is delivered either simultaneously or in a timed relation with a right ventricle pace as specified by a biventricular offset interval. The offset interval may be zero in order to pace both ventricles simultaneously, positive in order to pace the left ventricle after the right, or negative if the left ventricle is paced before the right. In many cases, pumping efficiency of the heart will be increased by simultaneous pacing of the ventricles with an offset of zero. However, it may be desirable in certain patients to pace one ventricle before the other in order to compensate for different conduction velocities in the two ventricles, and this may be accomplished by specifying a particular biventricular offset interval. The ventricles may be paced on an inhibited demand basis where the ventricular escape interval is restarted with either a ventricular pace or a right ventricular sense. The pacing mode may also include atrial tracking. In that case, a pair of ventricular paces are delivered after expiration of the AVI escape interval or expiration of the LRL escape interval, with ventricular pacing inhibited by a right ventricular sense that restarts the LRL escape interval or stops the AVI escape interval. Since the ventricular escape interval in this mode is reset or stopped by senses only from the right ventricle, a left ventricular protective period may be provided that starts with the occurrence of a left ventricular sense and lasts for a specified time. A left ventricular pace is then not permitted upon expiration of the escape interval if it would occur with the protective period.

A variation of biventricular pacing is to pace only the left ventricle (LV-only pacing). LV-only pacing may be advantageous where the conduction velocities within the ventricles are such that pacing only the left ventricle results in a more coordinated contraction by the ventricles than with conventional right ventricular pacing or biventricular pacing. LV-only pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval or stops the AVI escape interval. As with BV pacing, a left ventricular pace may be inhibited if a left ventricular sense occurs within a protective period prior to expiration of the ventricular escape interval. Since an inhibited left ventricular pace in this mode could result in a cardiac cycle with no pacing, the mode may be further modified such that a right ventricular safety pace is delivered if the left ventricular pace is inhibited and no right ventricular sense has occurred.

The histogram represents event frequencies that may be produced by a pacemaker. In one embodiment, these pacing and sensing frequencies are calculated. For example, where paces are delivered only to the right ventricle in accordance with a pacing mode based upon right ventricular senses, the number of senses and paces occurring through the right ventricular channel are counted during each cardiac cycle for a specified period of time, and each counted sense or pace is assigned to an interval bin representing the R-R interval for that cardiac cycle. The event frequencies, which are expressed as a percentage of total cardiac cycles during the specified period of time, are calculated as follows:

% RVS in bin=RVS count in bin/total RVS count+
total RVP count and

% RVP in bin=RVP count in bin/total RVS count+
total RVP count where RVS is a right ventricular sense and RVP is a right ventricular pace. The denominator in each case is the total count of right ventricular senses and paces during the specified period of time. Since in an inhibited demand pacing mode based upon right ventricular senses, right ventricular senses and right ventricular paces are mutually exclusive for a given cardiac cycle, the denominator represents the total number of cardiac cycles. The formula thus correctly computes the frequency of occurrence for each sense and pace in a particular interval bin.

In a pacemaker operating in a resynchronization pacing mode that paces the left ventricle, using the formula with a denominator as set forth above will not result in the correct event frequencies. In that case, using the above formula, the frequency of left ventricular senses would be:

% LVS in bin=LVS count in bin/total LVS count+total
LVP count which gives an incorrect frequency if right ventricular pacing only is programmed since the denominator degenerates to just the total LVS count. Or, if biventricular pacing is programmed with a right ventricular sense frequency of 100% and loss of the left ventricular sensing, the denominator becomes zero.

A pacemaker configured for biventricular pacing and sensing is operated in a mode where at least one ventricle is paced after expiration of a ventricular escape interval without receipt of a ventricular sense signal from one ventricle designated the primary ventricle, wherein the ventricular escape interval is restarted with either a ventricular pacing event or receipt of a sense signal from the primary ventricle. The ventricle other than the primary ventricle is designated the secondary ventricle. The number of senses and paces occurring through each ventricular channel during each cardiac cycle are counted for a specified period of time and with each counted sense or pace assigned to an interval bin representing the R-R interval for that cardiac cycle. The frequency of occurrence for the senses and paces in each interval bin over the specified period of time is then calculated by dividing the sense and pace count in each bin by a denominator equal to the sum of the total sense counts for the primary ventricle, the total pace counts for the primary ventricle, and the total pace counts for the secondary ventricle only for those cardiac cycles in which no pace was delivered to the primary ventricle.

In one embodiment, the pacing mode is such that the right ventricle is the primary ventricle and the left ventricle is the secondary ventricle. For example, only the left ventricle or both ventricles may be paced in an inhibited demand mode based only upon right ventricular senses with left ventricular senses used only to inhibit left ventricular paces. The formula for computing event frequencies then becomes:

% event in bin=event count in bin/total RVS count+
total RVP count+total LVP count where the LVP count includes only those left ventricular pacing events in which no right ventricular pace is delivered for that cardiac cycle. Incorporating both the RVP count and the LVP count into the denominator is beneficial for medical devices that switch autonomously between pacing modes (BV, RV and LV) to appropriately pace a patient under a variety of conditions. One condition under which the device may switch includes the detection of noise on one of the leads, in which case the device will pace from a lead without the noise. Another condition under which the device may switch includes a reversion to an ATR (Atrial Tachy Arrhythmia) mode, which occurs if or when the atrial rate is too high.

The reference made above with respect to a primary ventricle and a secondary ventricle also applies in a broader sense to a primary cardiac site and a secondary cardiac site. These sites include the following sets of sites: at least one left ventricle site and at least one right ventricle site; at least two left ventricle sites; at least two right ventricle sites; at least one left atrium site and at least one right atrium site; at least two left atrium sites; at least two right atrium sites; at least two sites in a first ventricle and at least one site in a second ventricle; and at least two sites in a first atrium and at least one site in a second atrium. One site within each set is a primary cardiac site, and another site within each set is a secondary cardiac site. A cardiac event distribution is determined by dividing an event count in bin by a denominator. The denominator is the sum of a total primary site sense count, a total primary site pace count, and a total secondary pace count. The secondary pace count includes only secondary pacing events in which no primary pace is delivered for a corresponding cardiac cycle.

The present subject matter, as described above, is not limited to any particular chamber of the heart, or combination of chambers, or to any particular paced cardiac event or sensed cardiac event. Rather, the present subject matter covers any electrode placement inside or outside of the right and left atriums and ventricles and to various combinations of cardiac events.

This application is intended to cover any adaptations or variations of the present invention. It is manifestly intended that this invention be limited only by the claims and equivalents thereof.

The invention claimed is:

1. A system for representing cardiac event data, comprising:
    a memory for storing cardiac event data for a first cardiac site and cardiac event data for a second cardiac site;
    a display device; and
    a processor adapted to communicate with the memory and the display device to display a histogram of the cardiac event data, wherein the histogram includes a plurality of histogram bins where the same histogram bin includes a representation of cardiac event data for the first cardiac site and a representation of cardiac event data for the second cardiac site.

2. The system of claim 1, wherein:
    the histogram of the cardiac event data includes a first statistical distribution for the first cardiac site and a second statistical distribution for the second cardiac site; and
    the representation of cardiac event data for the first cardiac site and cardiac event data for the second cardiac site includes a representation of at least a portion of the first statistical distribution for the first cardiac site and at least a portion of the second statistical distribution for the second cardiac site.

3. The system of claim 1, further comprising circuitry adapted to communicate with an implantable medical device, wherein the implantable medical device is adapted to acquire the cardiac event data, and wherein the system is adapted to retrieve the cardiac event data from the medical device to store the cardiac event data in the memory.

4. The system of claim 3, wherein the cardiac event data includes cardiac event data for a contralateral chamber sites.

5. The system of claim 3, wherein the cardiac event data for both a first cardiac site and a second cardiac site includes cardiac event data for a single cardiac camber chamber.

6. The system of claim 1, wherein the same histogram bin includes a representation of cardiac event data for the first cardiac site vertically adjacent to the cardiac event data for the second cardiac site.

7. The system of claim 1, wherein the same histogram bin includes a representation of cardiac event data for the first cardiac site horizontally adjacent to the cardiac event data for the second cardiac site.

8. The system of claim 1, wherein:
    the first cardiac site includes a first right ventricular site, and the second cardiac site includes a second right ventricular site; or
    the first cardiac site includes a first left ventricular site, and the second cardiac site includes a second left ventricular site; or
    the first cardiac site includes a first right atrial site, and the second cardiac site includes a second right atrial site; or
    the first cardiac site includes a first left atrial site, and the second cardiac site includes a second left atrial site.

9. A method implemented using processing circuitry executing stored executable instructions, the method comprising:
    retrieving cardiac event data for a first cardiac site and cardiac event data for a second cardiac site from a memory; and
    displaying a histogram of the cardiac event data for the first cardiac site and cardiac event data for the second cardiac site, wherein displaying the histogram includes:
    displaying a plurality of histogram bins; and
    representing cardiac event data for the first cardiac site and cardiac event data for the second cardiac site in the same histogram bin.

10. The method of claim 9, wherein:
    retrieving includes retrieving both paced event data and sensed intrinsic event data for both the first and second cardiac sites; and
    representing includes representing both paced event data and sensed intrinsic event data for the first cardiac site and both paced event data and sensed intrinsic event data for the second cardiac site in one of the plurality of histogram bins.

11. The method of claim 9, wherein representing includes representing the cardiac event data for the first cardiac site vertically adjacent within the same histogram bin to the cardiac event data for second cardiac site.

12. The method of claim 9, wherein representing includes representing the cardiac event data for the first cardiac site horizontally adjacent within the same histogram bin to the cardiac event data for second cardiac site.

13. A method implemented using processing circuitry executing stored executable instructions, the method comprising:
retrieving cardiac event data for both a first left ventricular site and a second left ventricular site from a memory; and
displaying a histogram of the cardiac event data, wherein displaying the histogram includes:
displaying a plurality of histogram bins; and
representing cardiac event data for the first left ventricular site and the second left ventricular site in the same histogram bin.

14. The method of claim 13, wherein:
retrieving includes retrieving a first statistical distribution for the first left ventricular site and a second statistical distribution for the second left ventricular site; and
representing includes representing at least a portion of the first statistical distribution for the first left ventricular site and at least a portion of the second statistical distribution for the second left ventricular site.

15. The method of claim 13, further comprising communicating with an implantable medical device, wherein the implantable medical device is adapted to acquire the cardiac event data, and wherein communicating with the implantable medical device includes retrieving the cardiac event data for the first left ventricular site and the cardiac event data for the second left ventricular site from the implantable medical device to store in the memory.

16. The method of claim 13, wherein:
retrieving includes retrieving both paced event data and sensed intrinsic event data for the first left ventricular site and both paced event data and sensed intrinsic data for the second left ventricular site; and
representing includes representing both paced event data and sensed intrinsic event data for the first left ventricular site and both paced event data and sensed intrinsic event data for the second left ventricular site in the same histogram bin.

17. A method implemented using processing circuitry executing stored executable instructions, the method comprising:
retrieving cardiac event data for a left ventricular site and cardiac event data for a right ventricular site from a memory; and
displaying a histogram of the cardiac event data for the left ventricular site and the cardiac event data for the right ventricular site, wherein displaying the histogram includes:
displaying a plurality of histogram bins; and representing the cardiac event data for the left ventricular site and the cardiac event data for the right ventricular site in the same histogram bin.

18. The method of claim 17, wherein:
retrieving includes retrieving a first statistical distribution for the left ventricular site and a second statistical distribution for the right ventricular site; and
representing includes representing at least a portion of the first statistical distribution for the left ventricular site and at least a portion of the second statistical distribution for the right ventricular site.

19. The method of claim 17, further comprising communicating with an implantable medical device, wherein the implantable medical device is adapted to acquire the cardiac event data, and wherein communicating with the implantable medical device includes retrieving the cardiac event data for the left ventricular site and the cardiac event data for the right ventricular site from the implantable medical device to store in the memory.

20. The method of claim 17, wherein:
retrieving includes retrieving both paced event data and sensed intrinsic event data for the left ventricular site and both paced event data and sensed intrinsic data for the right ventricular site; and
representing includes representing both paced event data and sensed intrinsic event data for the left ventricular site and both paced event data and sensed intrinsic event data for the right ventricular site in the same histogram bin.

21. A method implemented using processing circuitry executing stored executable instructions, the method comprising:
counting right ventricular sense (RVS) events, right ventricular pace (RVP) events, and left ventricular pace (LVP) events, wherein LVP events includes only left ventricular pacing events in which no right ventricular pace is delivered for a corresponding cardiac cycle;
adding the counted RVS events, the counted RVP events, and the counted LVP events to provide a sum;
determining a right ventricular cardiac event distribution and a left ventricular cardiac event distribution, wherein determining includes dividing an event count by the sum; and
displaying the right cardiac event distribution and the left ventricular cardiac event distribution.

22. The method of claim 21, wherein displaying includes displaying a histogram with a plurality of histogram bins in which the same histogram bin includes a representation for at least a portion of the right ventricular cardiac event distribution and a representation for at least a portion of the left ventricular cardiac event distribution.

23. The method of claim 22, wherein displaying includes representing the right cardiac event distribution vertically adjacent within the same histogram bin to the left cardiac event distribution.

24. The method of claim 22, wherein displaying includes representing the right cardiac event distribution horizontally adjacent within the same histogram bin to the left cardiac event distribution.

* * * * *